US00PP36024P2

(12) United States Plant Patent
Schulze et al.

(10) Patent No.: US PP36,024 P2
(45) Date of Patent: Jul. 23, 2024

(54) BLUEBERRY PLANT NAMED 'RB A140'

(50) Latin Name: *Vaccinium corymbosum*
Varietal Denomination: RB A140

(71) Applicant: Royal Berries, S.L.U., Almonte (ES)

(72) Inventors: Phillipp Schulze, Seville (ES); Ana Catarina Estrela da Costa, Matosinhos (PT)

(73) Assignee: Royal Berries, S.L.U., Almonte (ES)

( * ) Notice: Subject to any disclaimer, the term of this patent is extended or adjusted under 35 U.S.C. 154(b) by 0 days.

(21) Appl. No.: 18/523,419

(22) Filed: Nov. 29, 2023

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./156, 157
See application file for complete search history.

(56) References Cited

U.S. PATENT DOCUMENTS

PP34,620 P2 * 10/2022 Wheeler ..... Plt./157

* cited by examiner

*Primary Examiner* — Karen M Redden

(57) ABSTRACT

A new and distinct cultivar of Blueberry plant named 'RB A140' as described and shown herein. 'RB A140' is a commercial low chill tetraploid southern highbush blueberry (*Vaccinium*) variety intended for the fresh fruit market. 'RB A140' is well suited for production in low chill climates similar to Southern Spain.

8 Drawing Sheets

Latin name: *Vaccinium corymbosum.*
Common name: Blueberry.
Cultivar name: 'RB A140'.

BACKGROUND AND SUMMARY

Blueberries are a well-known fruit enjoyed by many throughout the world. The novel blueberry variety in this application, 'RB A140', is a new and distinct variety of southern highbush blueberry, botanically known as *Vaccinium corymbosum* L.

'RB A140' was the product of a controlled cross pollination carried out in Almonte, Huelva, Spain in 2008. The female parent (i.e., seed parent) was the proprietary variety 'Rocío' (U.S. Plant Pat. No. 20,374). The male parent (i.e., pollen parent) was the unreleased proprietary selection 'S03-08-03'. The parentage of the new variety 'RB A140' can be summarized as follows:

'Rocío' x 'S03-08-03'

'RB A140' was selected at the same location, Almonte, Huelva, Spain, in 2015 for its early fruit ripening and outstanding fruit quality characteristics in terms of organoleptic qualities, excellent sweet flavor and crunchy texture. It was initially asexually propagated by softwood cuttings from the original seedling in the same year and planted in first trials in 2017. Since then the new variety 'RB A140' has been reliably propagated asexually by softwood cuttings and was found to be stable; the propagated plants have retained the characteristics of the originally selected plant.

BRIEF DESCRIPTION OF THE PHOTOGRAPHS

The accompanying photographs show typical specimens in full color of the foliage, flowering and fruit of the new variety of 'RB A140' in Almonte, Huelva, Spain.

The colors in the photographs are as true as reasonably possible in color representations of this type. The color values cited in the detailed botanical description accurately describe the colors of the new blueberry variety.

DETAILED DESCRIPTION

Figure 1:
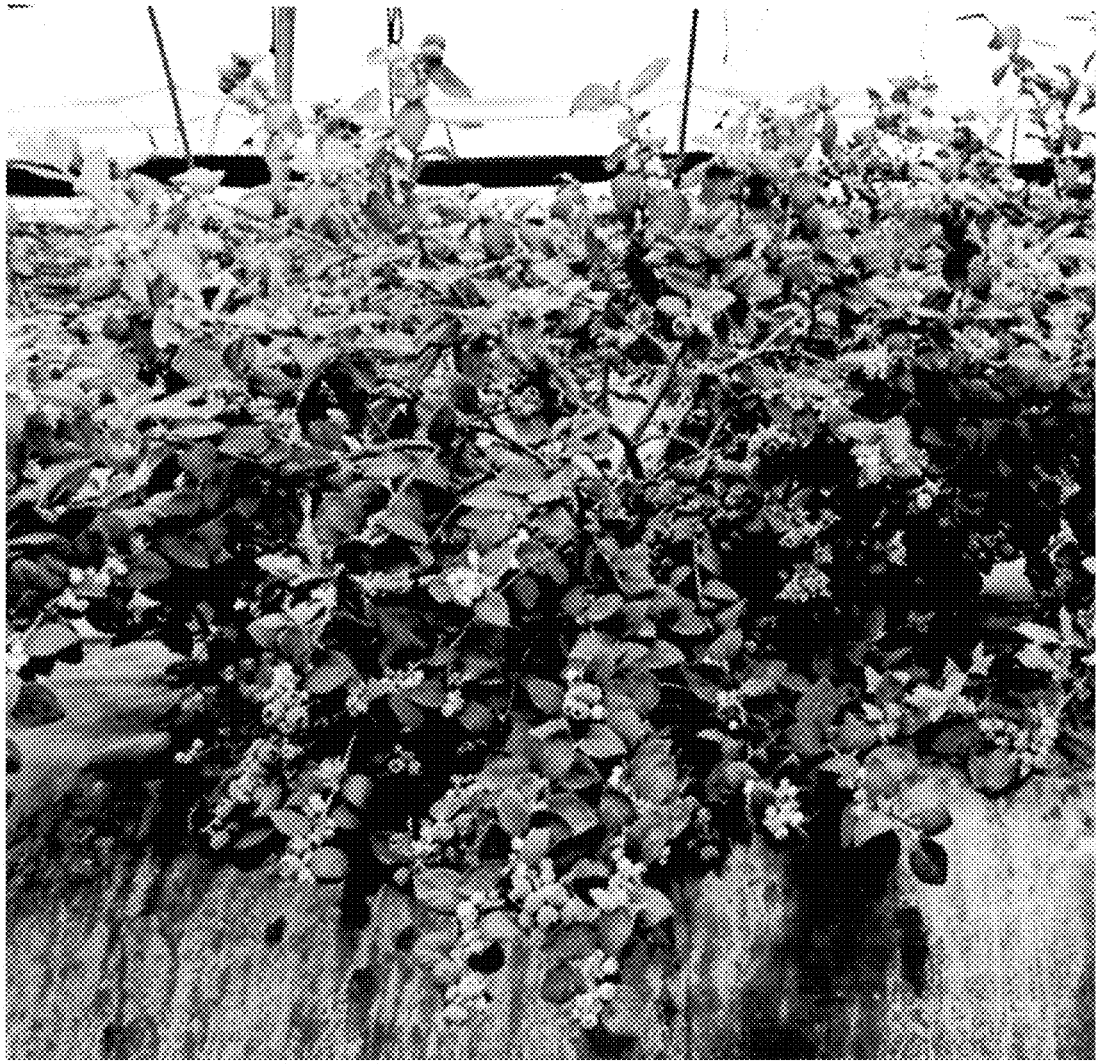
FIG. 1 is a photograph showing mature plants of 'RB A140' during flowering and fruit formation, and shows the overall bush shape and vigor.
Figure 2:
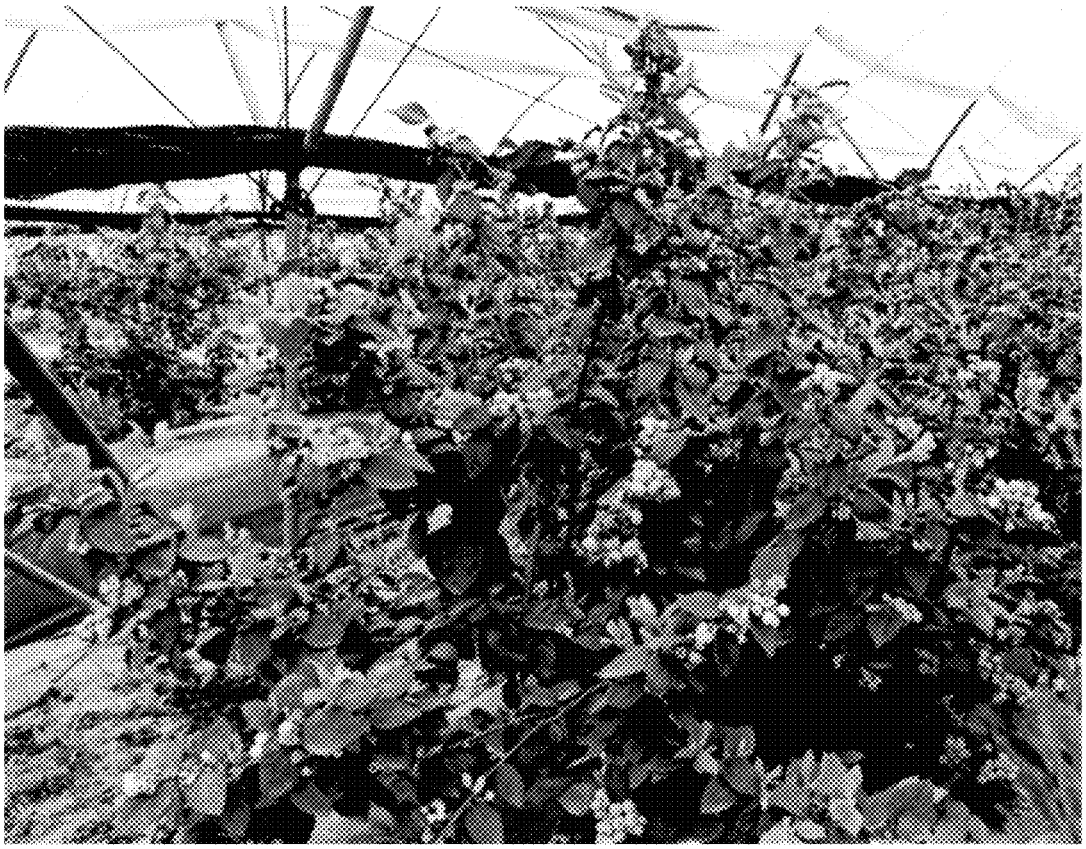
FIG. 2 is a photograph showing a mature plant of 'RB A140' during flowering and fruit formation, and shows the overall bush shape, leaf size and, color and structure of mature canes.
Figure 3:
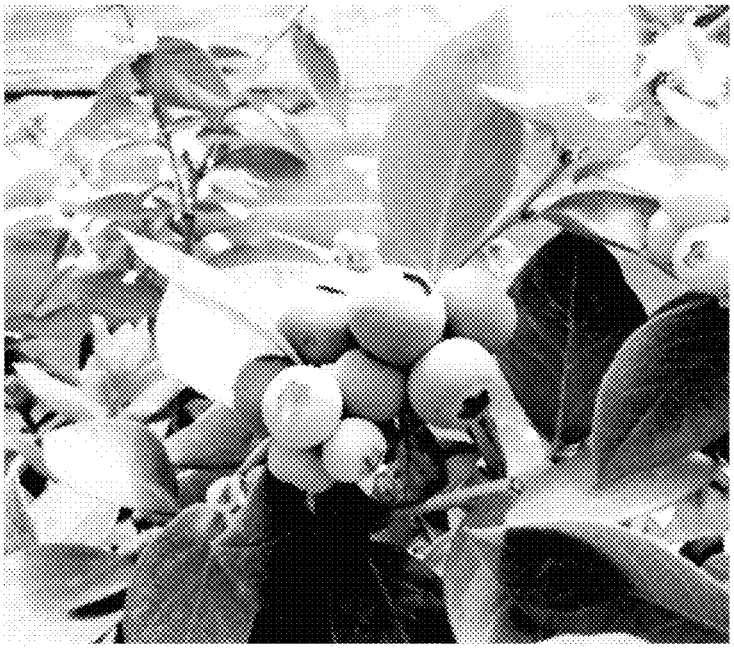
FIG. 3 is a photograph of fruit clusters of 'RB A140' during fruit ripening, showing the presentation of the fruit and cluster density.
Figure 4:
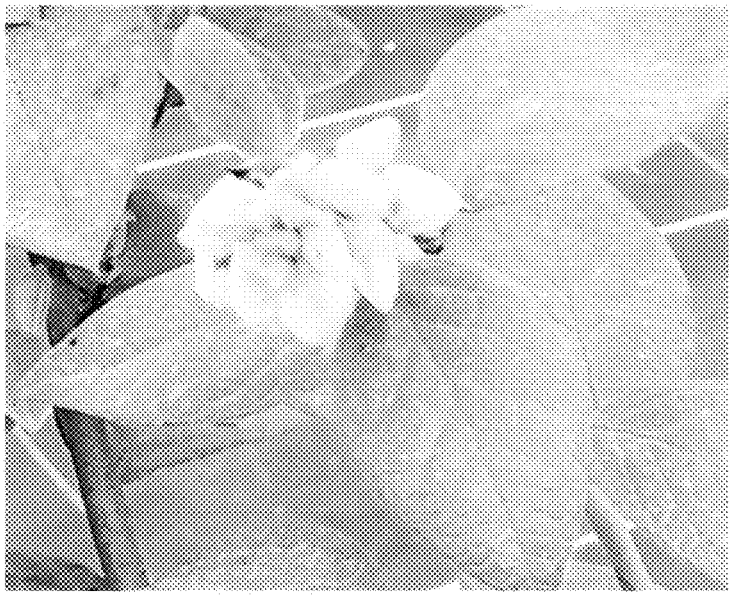
FIG. 4 is a close-up photograph of a flower cluster of 'RB A140', and shows the shape and color of flowers and floral buds in different stages.
Figure 5:
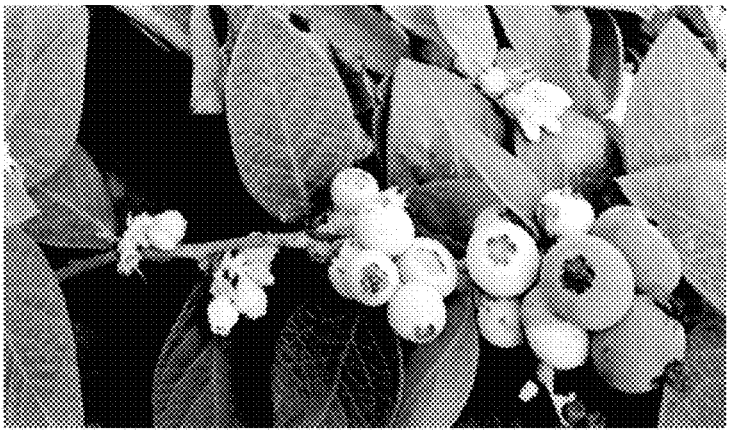
FIG. 5 is a close-up photograph of a flower and fruit cluster of 'RB A140', showing the size, shape and color of flowers and immature fruit in different stages.
Figure 6:
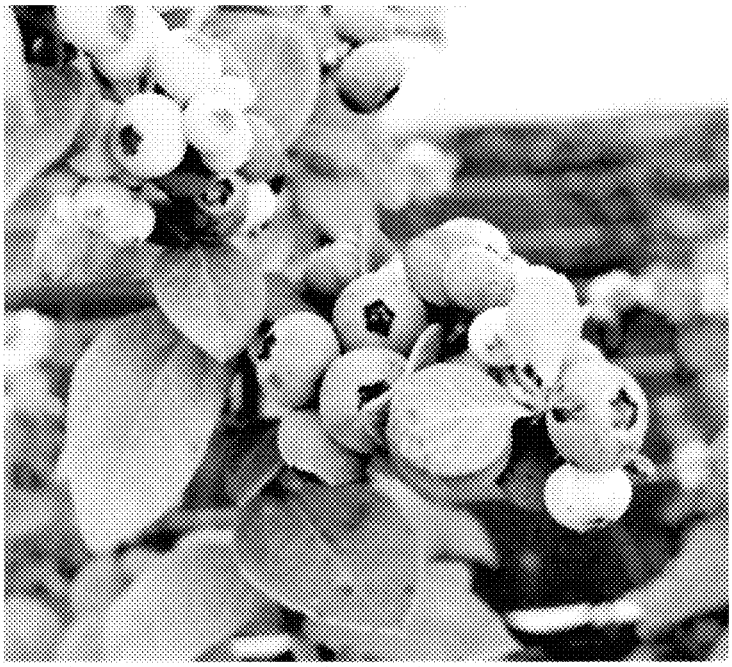
FIG. 6 is a close-up photograph of a fruit cluster of 'RB A140', showing the size, shape and color of immature fruit in different stages.
Figure 7:
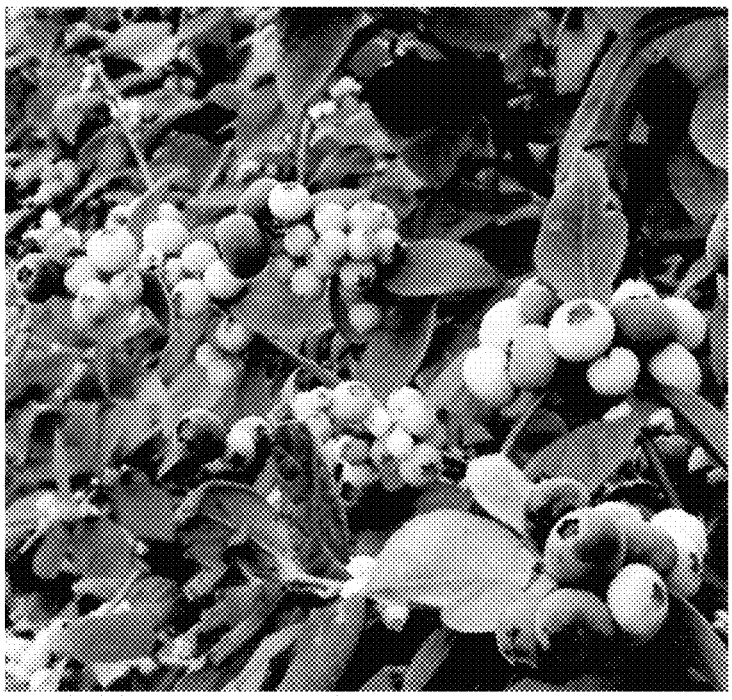
FIG. 7 is a close-up photograph of a fruit cluster of 'RB A140', showing the size, shape and color of ripe and unripe fruit.
Figure 8:
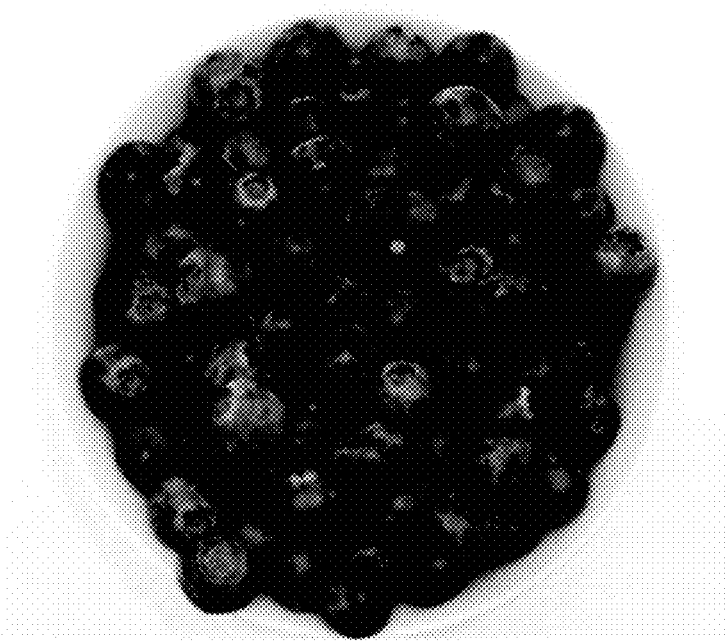
FIG. 8 is a close-up photograph of harvest fruit of 'RB A140'.

Note: statements of characteristics herein represent exemplary observations of the cultivar herein and will vary depending on time of year, location, annual weather, etc. Where dimensions, sizes, colors, and other characteristics are given, it is to be understood that such characteristics are approximations and averages.

The botanical descriptions herein were taken in Almonte, Huelva, Spain on 2 to 3-year-old plants during the years 2022 and 2023. The observations and measurements are average values calculated from a larger sample size.

Cultivar Name: 'RB A140'.

Classification:

Family: Ericaceae.

Botanical name: *Vaccinium corymbosum.*

Common name: Southern highbush blueberry

Parentage:

Female parent (please provide name or code): 'Rocío' (U.S. Plant Pat. No. 20,374).

Male parent (please provide name or code flower): 'S03-08-03' (unpatented).

The parentage of the new variety 'RB A140' can be summarized as follows:

'Rocío' x 'S03-08-03'

When compared to its female parent, 'Rocío', 'RB A140' has sweeter flavor, higher level of crunchiness and firmness and a similar production curve.

When compared to its male parent, the proprietary selection 'S03-08-03', 'RB A140' has an earlier harvest start, lighter fruit color, higher firmness, and sweeter flavor.

When compared to the southern highbush blueberry variety 'Sapphire' (U.S. Plant Pat. No. 11,829), 'RB A140' fruit color with bloom is light blue while 'Sapphire' fruit color with bloom is medium blue.

When compared to the southern highbush blueberry variety 'Legacy' (not patented), 'RB A140' has a early fruit ripening while 'Legacy' has a late fruit ripening.

General comments: 'RB A140' is a tetraploid southern highbush blueberry (*Vaccinium*) variety with a chill requirement of below 300 hours. It is best suited for production in low chill climates similar to Southern Spain. 'RB A140' is intended for the fresh fruit market. The following characteristics have been repeatedly observed in plants of the variety 'RB A140' growing in Almonte, Huelva, Spain and are determined to be unique characteristics of the new blueberry plant variety 'RB A140':

(a) an early fruit ripening;

(b) an excellent sweet flavor;

(c) a crunchy texture.

Color code observations are based upon The Royal Horticultural Colour Chart, 5th edition, published in 2007 by The Royal Horticultural Society, London, England.

Firmness was measured with a BioWorks FirmTech 2 Fruit Firmness Tester.

Plants of the 'RB A140' variety have not been observed under all possible environmental conditions to date. Accordingly, the phenotype may vary somewhat under different climatic conditions and cultural practices.

All observations and measurements were taken on 1-2 year old plants during the years 2022 and 2023.

Features of the variety:

Plant:

*Growth habit.*—Spreading.

*Height.*—Between 80-98 cm.

*Width.*—Between 90-115 cm.

*Vigor.*—Medium.

*Branching.*—High.

*Cold hardiness.*—Plant, flowers and fruit are hardy to −2° C. (Up to date, 'RB A140' has not been tested under cooler climate conditions.).

*Chilling requirement.*—<300 hours below 7° C.

*Resistance/tolerance to pest and disease.*—During the time of observations and to date, no exceptional sensitivities to any pest and disease were observed.

*Tendency toward evergreenness.*—High.

*Fruiting type.*—On 1-year-old and current season shoots.

*Productivity.*—High.

*Ease of propagation.*—'RB A140' has been reliably propagated asexually by softwood cuttings and was found to be stable.

Foliage:

*Time of beginning of bud burst.*—Approximately last week of January.

*Leaf shape.*—Ovate.

*Leaf length (without petiole).*—71 mm.

*Leaf width (at widest point).*—45 mm.

*Leaf length:width ratio.*—1.6.

*Leaf color of upper side.*—Green Group 137A.

*Leaf color of lower side.*—Yellow-Green Group N146B.

*Leaf margin.*—Entire.

*Leaf glaucosity on upper side.*—Present.

*Leaf pubescence on upper side.*—Absent.

*Leaf venation.*—Acuate, slightly reticulated.

*Leaf apices.*—Acute, approximately 55°.

*Leaf bases.*—Acute, approximately 60°.

*Petiole length.*—3.8 mm.

*Petiole color.*—Red-Purple Group 59B.

*Petiole pubescence.*—Absent.

Trunk and branches:

*Mature cane length.*—45 cm.

*Mature cane diameter.*—33.6 mm.

*Mature cane color.*—Grey-Brown Group N199B.

*Mature cane surface texture.*—Coarse.

*Immature cane length.*—49 cm.

*Immature cane diameter.*—27.4 mm.

*Immature cane color.*—Yellow-Green Group 144B.

*Immature cane surface texture.*—Smooth.

*Immature cane internode length.*—5 to 17 mm.

Flower:

*Time of beginning of flowering on 1-year-old shoot.*—Approximately 3rd week of November.

*Flowering period.*—Approximately 18 weeks.

*Number of flower clusters per fruiting shoot.*—7 to 20. Average: 15.7.

*Number of flowers per cluster.*—5 to 9.

*Fragrance.*—Absent.

*Shape.*—Globose.

*Immature flower color.*—Green-White Group 157B.

*Immature flower anthocyanin coloration.*—Present, low.

*Corolla color.*—White Group 155C.

*Corolla anthocyanin coloration.*—Absent.

*Corolla tube length.*—9.1 mm.

*Corolla tube width.*—7.7 mm.

*Corolla length:width ratio.*—1.2.

*Corolla aperture width.*—3.9 mm.

*Corolla ridges.*—Present.

*Number of petals.*—5.

*Petal length.*—10.2 mm.

*Petal width.*—4.2 mm.

*Peduncle color.*—Yellow-Green Group 144C.

*Pedicle length.*—3.4 mm to 16.2 mm.

*Pedicle width.*—1.4 mm.

*Calyx diameter with sepals.*—5.7 mm.
*Calyx color.*—Yellow-Green Group 144D.
*Style length.*—8.3 mm.
*Style shape.*—Bottle shaped.
*Pistils.*—Pistil: Anthers dorsifixed to filaments, no hairs on filaments or very low, filaments basifixed to calix; ratio pollensac:pollentube approximately 1:2.
*Pistil length.*—8.4 mm.
*Pistil color.*—Yellow-Green Group 150B.
*Ovary color.*—Yellow-Green Group 145D.
*Stamen length.*—5-6 mm.
*Number of stamen per flower.*—10.
*Filament color.*—Green-White Group 157B.
*Anther length.*—4.3 mm.
*Anther number.*—10.
*Anther color.*—Greyed-Orange Group 167A.
*Pollen abundance.*—Medium.
*Pollen color.*—Yellow-Orange Group 15D.
*Self-compatibility.*—Moderate-high.
*Time of beginning of flowering on current season shoot.*—Not usual.

Fruit:
*General.*—Fruit observations were taken at peak production during 2022 and 2023.
*Time of beginning of fruiting on* 1-*year-old shoot.*—Approximately 1st week of February.
*Time of end of fruiting on* 1-*year-old shoot.*—Approximately finishing May.
*Time of* 50% *fruiting on* 1-*year-old shoot.*—Approximately 15th of April.
*Fruiting period on* 1-*year-old shoot.*—Approximately 15 weeks.
*Time of beginning of fruiting on current season shoot.*—Not usual.
*Intensity of fruiting on current season shoots.*—Absent.
*Fruiting cluster density.*—Dense.
*Berry shape.*—Round-oblate.
*Berry calyx depth.*—Shallow.
*Berry calyx width.*—Medium.
*Berry attitude of sepals.*—Incurving.
*Berry height.*—15.2 mm.
*Berry width.*—18.5 mm.
*Berry height:width ratio.*—0.8.
*Berry weight.*—2.9 g.
*Surface color of unripe berry with wax* (*bloom*).—Yellow-Green Group 145C.
*Surface color of unripe berry without wax* (*bloom*).—Yellow-Green Group 145D.
*Surface color of mature berry with wax* (*bloom*).—Black Group 202B.
*Surface color of mature berry without wax* (*bloom*).—Black Group 203C.
*Surface wax* (*bloom*) *intensity.*—Low.
*Berry flesh color.*—Green-Yellow Group 1D.
*Picking scar.*—Medium-Small and dry.
*Firmness.*—Very High (275.4 gF/mm).
*Crunchiness.*—High.
*Texture.*—Crunchy and juicy.
*Sweetness.*—High (13.3 °Brix).
*Acidity.*—Medium (0.60 g/100 g titratable acidity).
*Sweetness:acidity ratio.*—31.2 (ratio B/A).
*Flavor.*—Very good, aromatic.
*Storage quality.*—Very good.

Seed:
*Number per berry.*—38.
*Dry weight* (1000 *seeds*).—0.68 g.
*Shape.*—Elliptic.
*Color.*—Greyed-Orange Group 165B.
*Length.*—1.3 to 2.0 mm.
*Width.*—0.4 to 0.6 mm.

Possible typical market uses: Fresh market.

What is claimed is:

1. A new and distinct cultivar of Blueberry plant named 'RB A140' as described and shown herein.

* * * * *